United States Patent [19]

Martin et al.

[11] Patent Number: 4,557,691
[45] Date of Patent: Dec. 10, 1985

[54] DENTAL PORCELAIN PASTE AND METHOD OF USING THE SAME

[75] Inventors: Brain Martin, Princeton Junction; Carlino Panzera, Belle Mead, both of N.J.

[73] Assignee: Johnson & Johnson Dental Products Company, East Windsor, N.J.

[21] Appl. No.: 642,281

[22] Filed: Aug. 20, 1984

Related U.S. Application Data

[63] Continuation-in-part of Ser. No. 484,015, Apr. 11, 1983, abandoned.

[51] Int. Cl.[4] .............................................. A61K 6/08
[52] U.S. Cl. .............................. 433/199.1; 433/202.1; 433/228.1; 523/116; 523/115; 523/117; 106/35; 528/950; 260/998.11
[58] Field of Search ............... 433/199, 201, 202, 217, 433/228; 260/998.11; 523/115, 116, 117

[56] References Cited

U.S. PATENT DOCUMENTS

| | | | |
|---|---|---|---|
| 2,792,628 | 5/1957 | Neumayer | 433/206 |
| 3,412,054 | 11/1968 | Milligan et al. | 260/18 |
| 4,250,277 | 2/1981 | Maries et al. | 260/998.11 |
| 4,264,640 | 4/1981 | Infante et al. | 264/19 |
| 4,329,490 | 8/1982 | Williams et al. | 560/89 |
| 4,347,174 | 8/1982 | Nagase et al. | 260/998.11 |
| 4,469,477 | 9/1984 | Potter | 433/199 |

Primary Examiner—John Kight
Assistant Examiner—Garnette D. Draper
Attorney, Agent, or Firm—Charles J. Metz

[57] ABSTRACT

A porcelain paste comprising a porcelain powder mixed with an aqueous colloidal dispersion of a urethane polymer. The paste can be applied as the first layer to a dental coping, and does not need to be fired prior to the addition of the body porcelain layers.

8 Claims, No Drawings

DENTAL PORCELAIN PASTE AND METHOD OF USING THE SAME

This application is a continuation-in-part of copending application Ser. No. 484,015, filed Apr. 11, 1983, now abandoned.

The invention relates to a dental porcelain paste composition that can be applied to a base, and which does not have to be fired before subsequent porcelain layers are applied on top of the porcelain layer of this invention. The invention also relates to a method of employing the dental porcelain paste.

BACKGROUND OF THE INVENTION

Today, most dental crowns and bridges are produced by a process which employs metal alloys and dental porcelains. The alloy frames, usually referred to as "copings", are prepared by the lost wax investment casting process. A variety of dental porcelains are then applied to the coping. The porcelain simulates the natural tooth both functionally and esthetically, and is ordinarily applied in two stages. First, an opaque porcelain layer (which is used to mask the coping) is applied as an aqueous paste to the surface of the metal coping, and this opaque layer is then dried and fired. Additional opaque porcelain is sometimes applied, dried, and fired if the initial application is either non-uniform or does not completely mask the alloy substructure. Once the opaque porcelain has been satisfactorily applied, the body porcelain layers, usually a gingival and an incisal porcelain, are applied as aqueous pastes and then dried and fired. A minimum of two firings is required; this includes a minimum of one firing for the opaque porcelain layer and a minimum of one firing for the body porcelain layers.

Recently, all-ceramic dental restorations have been introduced commercially. For instance, see Starling et al., U.S. Pat. No. 4,265,669. In an all-ceramic dental restoration, the metal coping is replaced with a ceramic base. In many cases, several layers of porcelain will be applied on top of the ceramic base. For instance, the ceramic base may be colored by application of a layer of a porcelain stain or by application of a layer of a pigmented dentino porcelain. In either case, one or more body porcelain layers will be applied on top of the stain or the dentino porcelain. Again, it is the usual practice to fire the restoration after the application of each layer, and as is the case with metal-based restorations, at least two firings are therefore needed; one for the stain or dentino porcelain and at least one for the body porcelain(s).

This invention provides a dental porcelain paste composition that does not have to be fired prior to the application of subsequent porcelain layers. As a result, both time and energy can be saved by practicing this invention since at least one firing procedure can be eliminated during the process for producing a dental crown or bridge.

BRIEF SUMMARY OF THE INVENTION

The dental porcelain paste composition of the invention comprises a dental porcelain powder and an aqueous colloidal urethane polymer dispersion. Preferably, the dental porcelain formulation has the same firing or maturing temperature as the subsequent body porcelain layers. In an important aspect of the invention, there is provided a package comprising the above-described dental porcelain paste composition in a suitable container.

The dental porcelain paste composition of the invention, when applied as a film or layer on a metal or ceramic base, dries rapidly (i.e., in about 20 minutes or less) in air at ambient temperatures (e.g., 25°–30° C.) to a water-resistant film. The urethane binder in the composition burns off when the dental prothesis is fired, without causing harmful voids, bubbles, cracks, or other similar defects. The paste composition itself has an acceptable shelf life, so that it can be pre-mixed by the manufacturer. This is advantageous for several reasons. First, the ingredients can be mixed in the optimum proportions. And second, the pre-mixed composition can be packaged in a dispenser/container designed to dispense only the quantity desired by the dental technician. Savings in material can therefore be realized by the user, because the user can readily dispense only the required amount.

THE PRIOR ART

Infante, in U.S. Pat. Nos. 4,046,732 and 4,264,640, describes earlier approaches toward the solution of the problem to which the subject invention relates. Infante describes dispersants for incorporation in both the opaque porcelain layer and the subsequent body porcelain layers in dental prostheses. These dispersants are aqueous solutions of various acrylic polymers. It is apparently an essential feature of Infante's invention that both the opaque porcelain layer and the body porcelain layers employ the dispersants. This can be disadvantageous because the body porcelain layer(s) are usually applied in much thicker layers than the opaque porcelain layer, and are therefore more apt to bubble or form harmful voids or cracks when they contain ingredients that must be burned off.

Hirschhorn, in U.S. Pat. No. 4,107,348, describes a resinous binder solution in water or water-alcohol, for use with the opaque porcelain layer in making a dental prosthesis.

DETAILED DESCRIPTION OF THE INVENTION

The porcelain powders that are used in the invention broadly constitute a known class of compositions. They are typically composed of silica, alumina, alkali metal oxides, alkaline earth metal oxides, and boron oxide, along with opacifiers and pigments, as needed. Illustrative opacifiers (which, in some cases, may also serve as white pigments) include tin (stannic) oxide, titanium dioxide, zirconium silicate, and calcium silicate, and illustrative pigments include yellow, pink, and brown pigments such as the oxides and chromate, vanadate, and manganate salts of vanadium, chromium, manganese, iron, cobalt, nickel, zirconium, praseodymium, and other ceramic pigments and coloring agents whose nature and mode of use are known in the art. The nature, specific compositions, and methods of preparation of such dental porcelains are known, and need not be repeated in detail here.

In one preferred aspect of the invention, the porcelain is an opaque porcelain selected to have a firing or maturing temperature of 1800° F., in order to match the firing temperatures of the body porcelain layers (gingival and incisal) that are to be applied on top of the opaque porcelain layer. The examples, below, give a specific illustration of an opaque porcelain formulation that meets this requirement.

The principal novelty of this invention resides in the use of an aqueous urethane polymer dispersion in conjunction with the dental porcelain powder. The resulting mixture, which is paste (often called a "slurry" in the dental art), in a preferred aspect is relatively stable and can therefore be pre-mixed by the manufacturer in the correct proportions, and can be packaged in convenient ready-to-use container/applicators such as flexible tubes and syringes.

Aqueous colloidal dispersions of urethane polymers are commercially available materials. Therefore, their nature and production are known in the art. For instance, they are described in the following U.S. patents, which are incorporated herein by reference:

Milligan et al., No. 3,412,054
Witt et al., No. 3,870,684
Hirooka et al., No. 3,983,058
Scriven et al., No. 4,066,591
Knachkamp et al., No. 4,172,191
Williams et al., No. 4,329,490

(These patents are merely illustrative of many that teach the preparation of aqueous colloidal urethane dispersions.)

The urethane polymers used to make the aqueous colloidal dispersions are substantially linear polymers that comprise the reaction products of polyether and/or polyester diols with organic diisocyanates. Useful polyether diols include polypropylene glycols, mixed polyethylene-polypropylene glycols, polytetramethylene ether glycols, and similar known materials. Useful polyesters include hydroxyl-terminated poly(ethylene adipate), poly(epsiloncaprolactone), and the like. Useful organic diisocyanates include aromatic diisocyanates such as tolylene diisocyanate, diphenylmethane diisocyanate ("MDI"), and the like, and aliphatic diisocyanates such as isophorone diisocyanate, bis(4-isocyanatocyclohexyl)methane, and the like.

The urethane polymers are produced by reacting the diol with diisocyanate in appropriate proportions. If desired the polyether and/or polyester diol may be reacted with a stoichiometric excess of organic diisocyanate to form an isocyanato-terminated prepolymer, which is then reacted with a difunctional chain extender. Difunctional chain extenders include diols such as ethylene glycol, diethylene glycol, 1,4-butane diol, and the like, and diamines such as ethylene diamine.

The ability of the urethane polymer to form stable aqueous colloidal dispersions is enhanced by incorporating hydrophilic groups in the polymer chains. Examples include carboxyl groups, which, when neutralized as with alkali, ammonia, or an amine, form such hydrophilic groups and thereby enhance the affinity of the polymer for water. Such carboxyl group functionality may be incorporated in the polymer chain, for instance, by using as the diol extender a dihydroxy-substituted carboxylic acid such as 2,2-bis(hydroxymethyl)propionic acid.

It has been found that both (a) the addition to the aqueous phase of small amounts of anions that form salts with calcium or barium that have low solubility in water (e.g., below about 0.5 weight percent), and (b) the maintenance of a slightly alkaline pH, e.g., 8 to 9, enhance the stability of the paste in some cases. Such anions are illustrated by oxalate, phosphate, silicate, borate, and tartrate. The alkaline pH helps to ensure that the urethane polymer will maintain its affinity for water and will therefore not tend to coagulate. The reason for the said anion's contributing to stability is less certain; it is probable that these anions serve to keep the aqueous phase substantially free of calcium and/or barium cations (and possibly other polyvalent metal cations) by immediately precipitating such cations as they are leached out of the porcelain powder. (Alkaline pH also helps here because the tendency of calcium and barium to leach out of the porcelain is less under alkaline conditions than under acid conditions.) Calcium and/or barium cations, even in very small quantities, could displace the solubilizing cation associated with the pendant carboxyl groups of the urethane polymer, and thereby tend to coagulate the urethane polymer.

Other ingredients that can be employed in the paste include dispersants, suspending agents, polar organic solvents, anti-foam agents, and biocides. Dispersants, which are employed to deter particle agglomeration, are illustrated by alkali metal polycarboxylate, sodium silicate, sodium polyphosphate, lecithin, and the like. Suspending agents are used to deter particles in the paste from settling. Illustrations include water-soluble high polymers such as alkal metal polycarboxylates, colloidal inorganic powders such as silica, clay, magnesium aluminum silicate, and magnesium silicate, and the like. (Some materials can act as both dispersants and suspending agents). The approximate proportions in which all these materials are employed are illustrated in the examples.

EXAMPLE 1

Preparation of Opaque Porcelain

In the preparation of the opaque porcelain, a potash feldspar and two silicate glasses are employed. These materials have the following compositions (in weight percent):

TABLE I

| Ingredient | Potash Feldspar | Silicate Glass A | Silicate Glass B |
|---|---|---|---|
| $SiO_2$ | 65.5 | 73.6 | 68 |
| $Al_2O_3$ | 18.6 | 1.3 | 3 |
| CaO | 0.07 | 5 | 5 |
| BaO | 0.01 | Trace | 2 |
| $Na_2O$ | 2.4 | 15.2 | 15 |
| $K_2O$ | 13.5 | 1.3 | 1 |
| $B_2O_3$ | — | — | 2 |
| MgO | — | 3 | 4 |

The opaque porcelain is composed of a blend of four components, as follows:

TABLE II

| | Weight Percent |
|---|---|
| 1. Component A | 60 |
| 2. Component B | 10 |
| 3. Silicate glass B | 10 |
| 4. Tin oxide (Harshaw 115) | 20 |

Component A is prepared from a mixture of 94 weight percent potash feldspar and 6 weight percent lithium carbonate, and Component B is prepared from a 50/50 (weight) mixture of the potash feldspar and silicate glass A. Components A and B are prepared as follows:

The raw materials are crushed to a fine powder, blended, ball milled for two hours (to pass through a 200 mesh screen), and then transferred to a dense alumina crucible. The charges are fired to 2250° F. for 4 hours, quenched in water, crushed, and then ball milled to form a powder fine enough to pass through a 165 mesh nylon screen.

Silicate glass B is also ball milled to pass through a 165 mesh nylon screen.

The four components are then blended to form an opaque porcelain having the following overall calculated composition:

TABLE III

| Ingredient | Weight Percent |
|---|---|
| $SiO_2$ | 52.5 |
| $Al_2O_3$ | 12.1 |
| CaO | 0.8 |
| BaO | 0.2 |
| MgO | 0.6 |
| $Na_2O$ | 3.6 |
| $K_2O$ | 8.6 |
| $Li_2O$ | 1.0 |
| $B_2O_3$ | 0.2 |
| $SnO_2$ | 20.0 |

The foregoing white opaque porcelain formulation is simply illustrative of those that can be used in the invention. It is formulated to have a coefficient of thermal expansion of about 14 to $15 \times 10^{-6}$ in./in./°C. (so that when pigments are added, in amounts of about 5 to 15 weight percent, the coefficient of thermal expansion will be about 13 to $14 \times 10^{-6}$ in./in./°C. to match dental alloy), and a firing or maturing temperature of about 1800° F. (to match the firing temperatures of the particular body porcelain layers used). If different coefficients of thermal expansion and/or maturing temperatures are desired, it is within the skill of the art, having knowledge of the teachings herein, to modify the formulation so as to obtain the desired properties. It is also relevant to mention that the use of a different grade of tin oxide than Harshaw 115 might necessitate a change in the proportions of the ingredients in the formulation. For instance, when Transelco 304 tin oxide is used, the following formulation has the desired coefficient of thermal expansion and maturing temperature:

Component A 65%
Component B 1.5%
Silicate Glass B 16.5%
Tin oxide (Transelco) 17%

Preparation of Paste

A paste is made from the following ingredients:

TABLE IV

| Component | Parts, by Weight |
|---|---|
| Water | 148 |
| Diammonium Phosphate | 2.8 |
| Colloidal Silica[1] | 3.5 |
| 30% aqueous ammonia, to pH 8.5 | 0.1–0.2 |
| Isopropyl alcohol | 10.5 |
| Water soluble thickener[2] | 1.26 |
| Opaque porcelain powder | 630 |
| Anti-foam agent[3] | 0.91 |
| Aqueous colloidal urethane polymer[4] | 51.8 |

[1]Cab-O-Sil M-5. The colloidal silica can be replaced with or supplemented by 1 to 2 parts of "Bentone LT", a colloidal clay.
[2]CPE-15 An acrylic polymer containing carboxyl functionality; supplied by Rohm & Haas.
[3]"Foamkill" 639AA (Crucible Chemical Company)
[4]"Neorez" R940- A 31 percent (by weight) solids aqueous colloidal dispersion of a polyether/tolylene diisocyanate urethane polymer containing corboxyl functionality which is neutralized with triethylamine. The dispersion contains a small amount of methyl ethyl ketone and N—methylpyrrolidone. It has a pH of 8.3 and a viscosity of 70 cps. It is supplied commercially by Polyvinyl Chemical Industries of Wilmington, Massachusetts.

The paste is made by the following procedure:

A bowl of a Hobart mixer is charged with half of the water in the formulation, the diammonium phosphate, and the colloidal silica, and the pH is adjusted to 8.5 by addition of aqueous ammonia. This mixture is mixed for half an hour until it forms a gel. While this gel is being formed, the water soluble thickener is added to the balance of the water, and a biocide (1,2-dibromo-2,4-dicyanobutane), in an amount of about 0.05 weight percent of the liquid components of the formulation, is dissolved in the isopropyl alcohol. After the silica has formed a gel, the aqueous solution of water soluble thickener and the biocide in isopropyl alcohol are added to the gel in the bowl of the Hobart mixer. With stirring, the porcelain powder is gradually added to the bowl, followed by the aqueous colloidal dispersion of urethane polymer and the anti-foam agent. The mixture is mixed for one hour in the Hobart mixer, and the viscosity is adjusted with water to a viscosity of 16,000 centipoises, measured on a Brookfield viscometer, model RVT, using spindle No. 6 at a speed of 50 rpm.

The above-described paste is coated on metallic coupons made of dental alloy and on dental copings, in coatings of about 8–10 mils thickness. The coatings are brushed on the coping or the coupon, and are then air dried for 20 minutes. A layer of body porcelain is then coated on top of the layer of opaque porcelain. For the coupons, the body porcelain layer is about 2 millimeters thick. On then coping, it is shaped to represent a dental crown, so that the thickness changes depending upon where it is on the crown. The coupons and copings are then fired using the body porcelain fusion cycle, which is the following:

The coupons and copings are placed in a vacuum oven at 1200° F., and the oven is heated at a heat-up rate of 90°–100° F. per minute to 1700° F. Air is then let in the oven, and it is heated at the same heat-up rate to 1800° F. When the oven reaches 1800° F., the copings and coupons are removed and are cooled in ambient air. In all cases, the samples show excellent adhesion of the porcelain to the metal, with no bubbling or cracking or any other defects apparent. The color is excellent, and the aesthetics of the porcelain layers are excellent.

EXAMPLES 2-4 AND CONTROL EXAMPLE 1

Three different pastes were made from the formulations displayed in Table V, below:

TABLE V

| Example | 2 | 3 | 4 |
|---|---|---|---|
| Water | 17 | 17 | 17 |
| 35% phosphoric acid | 0.85 | — | — |
| Oxalic acid | — | 0.3 | — |
| CPE 15 | 0.18 | 0.18 | 0.18 |
| 30% ammonia solution | 1.35 | 1.35 | 1.35 |
| R940 Urethane Dispersion | 7.38 | 7.38 | 7.38 |
| Porcelain powder | 90 | 90 | 90 |
| "Foamkill" 639AA | 0.13 | 0.13 | 0.13 |

These paste formulations were evaluated for water resistance by the following procedure. The formulation is brushed onto a metal panel in a thickness of about 8–10 mils. It is either allowed to air dry for 20 minutes in ambient air, or to air dry for 20 minutes in ambient air with an additional 5 minutes at 50° C. After this, the coatings are evaluated for water resistance by the following procedure: Water is poured onto the coating, and a soft brush is brushed across the coating and back again. This constitutes one double rub. Light pressure is applied while brushing. The end of the test is reached when metal shows through the coating, although the test is stopped at 50 double rubs. In Table VI below, the results of the test are shown for these three paste formulations, compared with a commercial acrylic formulation of the type described in the two Infante patents that are cited above.

TABLE VI

| Example | 2 | 3 | 4 | Commercial Acrylic Formulation |
|---|---|---|---|---|
| After 20 minute air dry | >50 | 40 | 20 | 3 |
| After 20-minute air dry + 5 mins. at 50° C.[5] | >50 | >50 | 18 | 1 |

As these results demonstrate, the paste formulation of this invention has significantly superior water resistance after drying than does the commercial acrylic formulation.
[5]The five-minute bake at 50° C. was used because the instructions that accompany the commercial acrylic formulation suggest such a low temperature bake. The low temperature bake is not needed with the compositions of this invention.

EXAMPLE 5

A preferred formulation for the porcelain paste of the invention is the following:

TABLE VII

| Component | Parts by weight |
|---|---|
| Porcelain Powder[1] | 100 |
| Water | 22.5 |
| Neo-Rez R940 | 8.19 |
| Isopropyl Alcohol | 1.08 |
| Cabosil M-5 | 0.355 |
| Silwet L7600[2] | 0.3125 |
| Acrysol CPE-15 | 0.229 |
| Bentone LT | 0.137 |
| Foamkill 639AA[3] | 0.0716 |
| Tektamer 38AD[4] | 0.0675 |
| Ammonia Solution | (to pH 8.5) |

[1]Same as Example 1.
[2]Wetting Agent - A polysiloxane-polyoxyalkylene block copolymer.
[3]Anti-foam Agent
[4]Biocide-1,2-dibromo-2,4-dicyanobutane.

The paste is preferably produced by the following procedure:

Deionized water (90 grams), Bentone LT (1.1 grams) and Cabosil M-5 (2.84 grams) were mixed in a Hobart mixer until a smooth gel was obtained. During the 15 minute mixing process, the pH was adjusted to 8.5-10 with 5 drops of ammonia solution (density=0.88 gm/cc).

Separately, Acrysol CPE-15 (1.83 grams) was diluted with deionized water (90 grams*), and while it was being stirred, ammonia solution was added dropwise to bring the pH to 8.5-10.
*This amount of water may be reduced to meet the viscosity target range of 15,000 to 20,000 cps.

With the Hobart mixer on low speed the following ingredients were added to gel in this order; isopropyl alcohol (8.66 grams), Tektamer 38 AD (0.54 grams) and the Acrysol solution. Then the porcelain powder was added incrementally and mixed until smooth. Intermittently, hand mixing is advantageous to incorporate porcelain caked on the sides and bottom of the bowl.

Finally, the following were added in this order; Neo-Rez R940 (65.5 grams), Foamkill 639AA (0.57 grams) and Silwet L-7600 (2.5 grams). This was mixed until smooth.

A sample was tested for dispersion quality on a Hegmann grind gauge, which measures agglomerate size; it passed 85μ.

The product was covered with plastic film and allowed to stand 24 hours. Then it was mixed by hand and the viscosity measured in the Brookfield RVT Viscometer, spindle #6 at 50 rpm. The viscosity (16,700 cps) fell in the target range of 15,000-20,000 cps without further water addition.

EXAMPLE 6

A dental porcelain paste suitable for use as a porcelain stain for a ceramic base is made by a procedure analogous to that described in Example 5 from the following formulation:

TABLE VIII

| Compound | Parts, by weight |
|---|---|
| Bentone LT | 0.44 |
| Cabosil M-5 | 1.14 |
| Acrysol CPE-15 | 0.73 |
| Isopropyl Alcohol | 3.56 |
| Neo Rez R940 | 26.2 |
| Silwet L7600 | 1.3 |
| Yellow Porcelain Stain | 209 |
| Ammonia | to pH 8.5 |

(1) The yellow porcelain stain is a mixture of 22.7 weight percent tin vanadate pigment, 9.3 weight percent zirconium silicate opacifier, and 68 weight percent silicate glass B (see Table I above).

The yellow porcelain stain described above in Table VIII is a very intense yellow stain. A more typical porcelain stain composition has the following formulation:

| | Parts, by Weight |
|---|---|
| $K_2O$ | 0.3 |
| $Na_2O$ | 5.9 |
| CaO | 0.8 |
| $B_2O_3$ | 9.2 |
| $Al_2O_3$ | 10.7 |
| $SiO_2$ | 72.7 |
| SrO | 0.15 |
| BaO | 0.8 |
| Pigment | 1 ± ¼ |

A typical dentino porcelain composition, which can be used as a layer on a ceramic core, has the following formulation:

| | Parts, by Weight |
|---|---|
| $K_2O$ | 4 |
| $Na_2O$ | 4.5 |
| CaO | 2.7 |
| $B_2O_3$ | 7.9 |
| $Al_2O_3$ | 9.4 |
| $SiO_2$ | 71.5 |
| Opacifier | 10 ± 5 |
| Pigments | 1 ± 0.5 |

What is claimed is:

1. A paste suitable for applying to a metal or ceramic dental base as a porcelain layer, which layer does not need to be fired prior to addition of a body porcelain layer, which paste comprises a porcelain powder and an aqueous colloidal dispersion of a urethane polymer, wherein said urethane polymer contains carboxyl groups, and wherein the carboxyl groups are neutralized with alkali metal, ammonia, or amine.

2. The paste of claim 1 wherein the aqueous phase contains an anion that forms a salt with calcium or barium that has low solubility in water.

3. The paste of claim 2 wherein said anion is phosphate, oxalate, or a mixture thereof.

4. The paste of claim 1 wherein said paste contains a small amount of a suspending agent and a dispersant.

5. The paste of claim 1 wherein the porcelain powder is an opaque porcelain powder.

6. The paste of claim 1 wherein the porcelain powder is a porcelain stain.

7. The paste of claim 1 wherein the porcelain powder is a dentino porcelain.

8. A package comprising the paste of claim 1 in a suitable applicator/container.

* * * * *